US006180639B1

(12) United States Patent
Coates et al.

(10) Patent No.: US 6,180,639 B1
(45) Date of Patent: *Jan. 30, 2001

(54) 1,3-OXATHIOLANE NUCLEOSIDE ANALOGUES

(75) Inventors: Jonathan Allan Coates; Ian Martin Mutton; Charles Richard Penn; Christopher Williamson; Richard Storer, all of Greenford (GB)

(73) Assignee: BioChem Pharma Inc., Laval (CA)

(*) Notice: Under 35 U.S.C. 154(b), the term of this patent shall be extended for 0 days.

This patent is subject to a terminal disclaimer.

(21) Appl. No.: 07/835,964

(22) PCT Filed: May 2, 1991

(86) PCT No.: PCT/GB91/00706

§ 371 Date: Feb. 20, 1992

§ 102(e) Date: Feb. 20, 1992

(87) PCT Pub. No.: WO91/17159

PCT Pub. Date: Nov. 14, 1991

(30) Foreign Application Priority Data

May 2, 1990 (GB) .................................................. 9009861

(51) Int. Cl.⁷ ....................... A61K 31/505; C07D 411/04
(52) U.S. Cl. ............................. 514/274; 514/43; 514/49; 514/50
(58) Field of Search .................... 544/317, 274, 544/43, 49, 50

(56) References Cited

U.S. PATENT DOCUMENTS

| | | | |
|---|---|---|---|
| 4,336,381 | 6/1982 | Nagata et al. ........................ | 544/313 |
| 5,039,567 | 8/1991 | Tyrrell et al. ........................ | 514/45 |
| 5,047,407 | 9/1991 | Belleau et al. ........................ | 514/274 |
| 5,204,466 | * 4/1993 | Liotta et al. ........................ | 544/314 |
| 5,466,806 | * 11/1995 | Belleau et al. ........................ | 544/310 |
| 5,539,116 | * 7/1996 | Liotta ................................. | 544/317 |
| 5,627,186 | 5/1997 | Cameron et al. ..................... | 514/274 |
| 5,756,478 | 5/1998 | Cheng et al. ........................ | 514/45 |
| 5,859,021 | 1/1999 | Cameron et al. ..................... | 514/274 |
| 5,869,461 | 2/1999 | Cheng et al. ........................ | 514/43 |

FOREIGN PATENT DOCUMENTS

| | | |
|---|---|---|
| 0 212 409 B1 | 3/1987 | (EP) . |
| 0 302 760 | 6/1988 | (EP) . |
| 0 382 526 A2 | 2/1989 | (EP) . |
| 0 337 713 A2 | 10/1989 | (EP) . |
| 0 349 242 A2 | 1/1990 | (EP) . |
| 0 363 582 A1 | 4/1990 | (EP) . |
| 0 421 777 A1 | 4/1991 | (EP) . |
| 2 063 257 | 6/1981 | (GB) . |
| 2 230 266 | 10/1990 | (GB) . |
| WO 89/04662 | 6/1989 | (WO) . |
| WO 90/12023 | 10/1990 | (WO) . |
| WO 91/00282 | 1/1991 | (WO) . |
| WO 91/01326 | 2/1991 | (WO) . |
| WO 91/11186 | 8/1991 | (WO) . |

OTHER PUBLICATIONS

Baba et al., "Both 2',3'–Dideoxythymidine and its 2',3'–Unsaturated Derivative (2',3'–Dideoxythymidinene) are Potent and Selective Inhibitors of Human Immunodeficiency Virus Replication in vitro", *Biochemical and Biophysical Research Communications*, 142(1) pp. 128–134 (1987) ("Baba").

Balzarini et al., "Potent and Selective Anti–HTLV–III/LAV Activity of 2',3'–Dideoxycytidinene, the 2',3'–Unsaturated Derivative of 2',3'–dideoxycytidine", *Biochemical and Biophysical Research Communications*, 140(2), pp. 735–742 (1986) ("Balzarini").

Belleau et al., "Design And Activity Of A Novel Class Of Nucleoside Analogs Effective Against HIV–1", Fifth International Conference on AIDS, Montreal, Canada, Abstract T.C.O. 1 (1989) ("Belleau").

Carlisle et al., "Cellular Pharmacology Of The Anti–HIV Agent BCH–189 (2'Deoxy–3'–Thiacytidine) In Human Peripheral Blood Mononuclear Cells (PBMC)", *American Association for Cancer Research Proceedings*, 31, abstract 2435, (1990) ("Carlisle").

Gosselin et al., "Systematic Synthesis And Biological Evaluation Of α– and β–D–Lyxofuranosyl Nucleotides Of The Five naturally Occurring Nucleic Acid Bases", *J. Med. Chem.*, 30, pp. 1270–1278 (1987) ("Gosselin").

Herdewijn et al., "3'–Substituted 2',3'–Dideoxynucleoside Analogues as Potential as Potential anti–HIV (HTLV–III/LAV) Agents", *J. Med. Chem.*, 30, pp. 1270–1278 (1987) ("Herdewijn").

Lin et al., "Synthesis and Antiviral Activity of Various 3'Azido, 3'–Amino, 2',3'–Unsaturated, and 2',3'–Dideoxy Analogues of Pyrimidine Deoxyribonucleosides against Retroviruses", *J. Med. Chem.*, 30, pp. 440–444 (1987) ("Lin").

Mitsuya et al., "3'–Azido–3'–Deoxythymidine (BW A509U): An Antiviral Agent that Inhibits the Infectivity and Cytopathic Effect of Human T–Lymphotropic Virus Type III/Lymphadenopathy–Associated Virus in vitro", Proc. Natl. Acad. Sci. USA, 82, pp. 7096–7100 (1986) ("Mitsuya –1").

Mitsuya et al. "Inhibition of the in vitro Infectivity and Cytopathic Effect of Human T–Lymphotrophic Virus Type III/Lymphadenopathy–Associated Virus (HTLV–III/LAV) by 2', 3'–Dideoxynucleosides", Proc. Natl. Acad. Sci. USA, 83, pp. 1911–1915 (1986) ("Mitsuya–2").

(List continued on next page.)

*Primary Examiner*—Frederick Krass
(74) *Attorney, Agent, or Firm*—Millen, White, Zelano & Branigan, P.C.

(57) ABSTRACT

(–)-4-amino-1-(2-hydroxymethyl-1,3-oxathiolan-5-yl)-(1H)-pyrimidin-2-one, its pharmaceutically acceptable derivatives, pharmaceutical formulation thereof, methods for its preparation and its uses as an antiviral agent are described.

64 Claims, No Drawings

OTHER PUBLICATIONS

Wainberg et al., "Anti–HIV Activity, Toxicity And Pharmacokinetics Of Totally Novel Nucleoside Analogs," Fifth International Conference on AIDS, Montreal, Canada, Abstract M.C.P. 63, p. 552, (1989) ("Wainberg –1").

Wainberg et al., "Characterization Of AZT–Resistant Isolates Of HIV–1: Susceptibility To Deoxythiacytidine And Other Nucleosides", Sixth International Conference on Aids, San Francisco, California, vol. 3, Abstract S.B.87, p. 117 (1990) ("Wainberg –2").

Clereq, AIDS Research and Human Retroviruses, vol. 8, No. 2, 1992, pp. 119–134.*

Beach et al., "Synthesis of Enantiomerically Pure (2'R, 5'S)–(–)–1–[Hydroxymethyl)oxathiolan–5–yl]cytosine as a Potent Antiviral Agent against Hepatitis B Virus (HBV) and Human Immunodeficiency Virus (HIV)," *J. Org. Chem.* 1992, 57, 2217–2219.

Chang et al., "Deoxycytidine Deaminase–resistant Stereoisomer Is the Active Form of $(^{+-})$ –2', 3'Dideoxy–3'–thiacytidine in the Inhibition of Hepatitis B Virus Replication," *Journal of Biological Chemistry*, Jul. 15, 1992, vol. 267, No. 20.

Schinazi et al., "Activities of the Four Optical Isomers of 2',3'–Dideoxy–3'–Thiacytidine (BCH–189)against Human Immunodeficiency Virus Type 1 in Human Lymphocytes," *Antimicrobial Agents& Chemotherapy*, Mar. 1992, vol. 36, No. 3.

Enantimers, Racemates and Resolutions, J. Jacques et al, John Wiley & Sons (1981).*

* cited by examiner

1,3-OXATHIOLANE NUCLEOSIDE ANALOGUES

This application is a con of PCT/6891/00706, filed May 2, 1991.

The present invention relates to nucleoside analogues and their use in medicine. More specifically the invention is concerned with 1,3-oxathiolane nucleoside analogues, pharmaceutical formulations thereof and the use thereof in the treatment of viral infections.

The compound of formula (I)

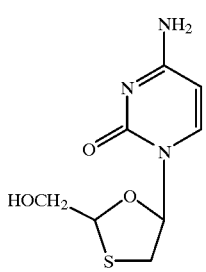

(I)

also known as BCH-189 or NGPB-21 has been described as having antiviral activity in particular against the human immunodeficiency viruses (HIV's), the causative agents of AIDS (5th Anti-Aids Conference, Montreal, Canada Jun. 5th–9th 1989: Abstracts T.C.O.1 and M.C.P. 63: European Patent Application Publication No. 0382562). The compound of formula (I) is a racemic mixture of the two enantiomers of formulae (I-1) and (I-2):

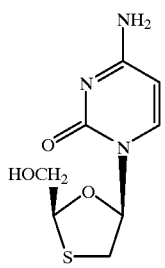

(I-2)

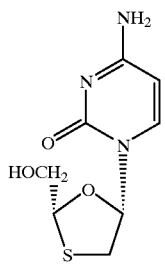

(I-1)

and was described and tested in the form of its racemate. The only compound currently approved for the treatment of conditions caused by HIV is 3'-azido-3'-deoxythymidine (AZT, zidovudine, BW 509U). However, this compound has a significant side-effect liability and thus either cannot be employed or, once employed, may have to be withdrawn in a significant number of patients. There is in consequence a continuing need to provide compounds which are effective against HIV but with a concomitant significantly better therapeutic index.

We have now found that, surprisingly, enantiomers of the compound of formula (I) are equipotent against HIV but that one of the enantiomers (the (−)-enantiomer) has considerably lower cytotoxicity than the other enantiomer. There is thus provided in a first aspect of the invention the (−) (or laevorotatory) enantiomer of the compound of formula (I) and pharmaceutically acceptable derivatives thereof.

The (−) enantiomer has the chemical name (−)-cis-4-Amino-1-(2-hydroxymethyl-1,3-oxathiolan-5-yl)-(1H)-pyrimidin-2-one (hereinafter compound (A)). It has the absolute stereochemistry of the compound of formula (I-1) which has the name (2R,cis))-4-amino-1-(2-hydroxymethyl-1,3-oxathiolan-5-yl)-(1H)-pyrimidin-2-one.

Preferably Compound A is provided substantially free of the corresponding (+)-enantiomer, that is to say no more than about 5% w/w of the (+)-enantiomer, preferably no more than about 2%, in particular less than about 1% w/w is present.

By "a pharmaceutically acceptable derivative" is meant any pharmaceutically acceptable salt, ester, or salt of such ester, of compound (A) or any other compound which, upon administration to the recipient, is capable of providing (directly or indirectly) compound (A) or an antivirally active metabolite or residue thereof.

It will be appreciated by those skilled in the art that compound (A) may be modified to provide pharmaceutically acceptable derivatives thereof, at functional groups in both the base moiety and at the hydroxymethyl group of the oxathiolane ring. Modification at all such functional groups are included within the scope of the invention. However of particular interest are pharmaceutically acceptable derivatives obtained by modification of the 2-hydroxymethyl group of the oxathiolane ring.

Preferred esters of compound (A) include the compounds in which the hydrogen of the 2-hydroxy-methyl group is replaced by an acyl function R—C— in which the non-carbonyl moiety R of the ester is selected from hydrogen, straight or branched chain alkyl (e.g. methyl, ethyl, n-propyl, t-butyl, n-butyl), alkoxyalkyl (e.g. methoxymethyl), aralkyl (e.g. benzyl), aryloxyalkyl (e.g. phenoxymethyl), aryl (e.g. phenyl optionally substituted by halogen, $C_{1-4}$ alkyl or $C_{1-4}$ alkoxy); sulphonate esters such as alkyl- or aralkylsulphonyl (e.g. methanesulphonyl); amino acid esters (e.g. L-valyl L-isoleucyl) and mono-, di- or tri-phosphate esters.

With regard to the above described esters, unless otherwise specified, any alkyl moiety present advantageously contains 1 to 16 carbon atoms, particularly 1 to 4 carbon atoms. Any aryl moiety present in such esters advantageously comprises a phenyl group.

In particular the esters may be a $C_{1-16}$alkyl ester, an unsubstituted benzyl ester or a benzyl ester substituted by at least one halogen (bromine, chlorine, fluorine or iodine), $C_{1-6}$alkyl, $C_{1-6}$alkoxy, nitro or trifluoromethyl groups.

Pharmaceutically acceptable salts of the compound (A) include those derived from pharmaceutically acceptable inorganic and organic acids and bases. Examples of suitable acids include hydrochloric, hydrobromic, sulphuric, nitric, perchloric, fumaric, maleic, phosphoric, glycollic, lactic, salicylic, succinic, toluene-p-sulphonic, tartaric, acetic, citric, methanesulphonic, formic, benzoic, malonic, naphthalene-2-sulphonic and benzenesulphonic acids. Other acids such as oxalic, while not in themselves pharmaceutically acceptable, may be useful as intermediates in obtaining the compounds of the invention and their pharmaceutically acceptable acid addition salts.

Salts derived from appropriate bases include alkali metal (e.g. sodium), alkaline earth metal (e.g. magnesium), ammonium and $NR_4$— (where R is $C_{1-4}$alkyl) salts.

References hereinafter to a compound according to the invention include both the compound (A) and its pharmaceutically acceptable derivatives.

The compounds of the invention either themselves possess antiviral activity and/or are metabolizable to such compounds. In particular these compounds are effective in inhibiting the replication of retroviruses, including human retroviruses such as human immunodeficiency viruses (HIV's), the causative agents of AIDS.

There is thus provided as a further aspect of the invention compound (A) or a pharmaceutically acceptable derivative thereof for use as an active therapeutic agent in particular as an antiviral agent, for example in the treatment of retroviral infections.

In a further or alternative aspect there is provided a method for the treatment of a viral infection, in particular an infection caused by a retrovirus such as HIV, in a mammal including man comprising administration of an effective amount of compound (A) or a pharmaceutically acceptable derivative thereof.

There is also provided in a further or alternative aspect use of compound (A) or a pharmaceutically acceptable derivative thereof for the manufacture of a medicament for the treatment of a viral infection.

The compounds of the invention are also useful in the treatment of AIDS related conditions such as AIDS-related complex (ARC), progressive generalised lymphadenopathy (PGL), AIDS-related neurological conditions (such as dementia or tropical paraparesis), anti-HIV antibody positive and HIV-positive conditions, Kaposi's sarcoma, thrombocytopenia purpurea and associated opportunistic infections for example *Pneumocystis carinii*.

The compounds of the invention are also useful in the prevention of progression to clinical illness of individuals who are anti-HIV antibody or HIV-antigen positive and in prophylaxis following exposure to HIV.

The compound (A) or pharmaceutically acceptable derivatives thereof may also be used for the prevention of viral contamination of physiological fluids such as blood or semen in vitro.

It will be appreciated by those skilled in the art that reference herein to treatment extends to prophylaxis as well as the treatment of established infections or symptoms.

It will be further appreciated that the amount of a compound of the invention required for use in treatment will vary not only with the particular compound selected but also with the route of administration, the nature of the condition being treated and the age and condition of the patient and will be ultimately at the discretion of the attendant physician or veterinarian. In general however a suitable dose will be in the range of from about 0.1 to about 750 mg/kg of bodyweight per day preferably in the range of 0.5 to 60 mg/kg/day, most preferably in the range of 1 to 20 mg/kg/day.

The desired dose may conveniently be presented in a single dose or as divided doses administered at appropriate intervals, for example as two, three, four or more sub-doses per day.

The compound is conveniently administered in unit dosage form; for example containing 10 to 1500 mg, conveniently 20 to 1000 mg, most conveniently 50 to 700 mg of active ingredient per unit dosage form.

Ideally the active ingredient should be administered to achieve peak plasma concentrations of the active compound of from about 1 to about 75 $\mu$M, preferably about 2 to 50 $\mu$M, most preferably about 3 to about 30 $\mu$M. This may be achieved, for example, by the intravenous injection of a 0.1 to 5% solution of the active ingredient, optionally in saline, or orally administered as a bolus containing about 1 to about 100 mg of the active ingredient. Desirable blood levels may be maintained by a continuous infusion to provide about 0.01 to about 5.0 mg/kg/hour or by intermittent infusions containing about 0.4 to about 15 mg/kg of the active ingredient.

While it is possible that, for use in therapy, a compound of the invention may be administered as the raw chemical it is preferable to present the active ingredient as a pharmaceutical formulation.

The invention thus further provides a pharmaceutical formulation comprising compound (A) or a pharmaceutically acceptable derivative thereof together with one or more pharmaceutically acceptable carriers therefor and, optionally, other therapeutic and/or prophylactic ingredients. The carrier(s) must be 'acceptable' in the sense of being compatible with the other ingredients of the formulation and not deleterious to the recipient thereof.

Pharmaceutical formulations include those suitable for oral, rectal, nasal, topical (including buccal and sub-lingual), vaginal or parenteral (including intramuscular, subcutaneous and intravenous) administration or in a form suitable for administration by inhalation or insufflation. The formulations may, where appropriate, be conveniently presented in discrete dosage units and may be prepared by any of the methods well known in the art of pharmacy. All methods include the step of bringing into association the active compound with liquid carriers or finely divided solid carriers or both and then, if necessary, shaping the product into the desired formulation.

Pharmaceutical formulations suitable for oral administration may conveniently be presented as discrete units such as capsules, cachets or tablets each containing a predetermined amount of the active ingredient; as a powder or granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds according to the invention may also be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilising and/or dispersing agents. Alternatively, the active ingredient may be in powder form, obtained by aseptic isolation of sterile solid or by lyophilisation from solution, for constitution with suitable vehicle, e.g. sterile, pyrogen-free water, before use.

For topical administration to the epidermis the compounds according to the invention may be formulated as ointments, creams or lotions, or as a transdermal patch. Ointments and creams may, for example, be formulated with a aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Formulations suitable for topical administration in the mouth include lozenges comprising active ingredient in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Pharmaceutical formulations suitable for rectal administration wherein the carrier is a solid are most preferably presented as unit dose suppositories. Suitable carriers include cocoa butter and other materials commonly used in the art, and the suppositories may be conveniently formed by admixture of the active compound with the softened or melted carrier(s) followed by chilling and shaping in moulds.

Formulations suitable for vaginal administration may be presented as pessaries, tampons, creams, gels, pastes, foams or sprays containing in addition to the active ingredient such carriers as are known in the art to be appropriate.

For intra-nasal administration the compounds of the invention may be used as a liquid spray or dispersible powder or in the form of drops.

Drops may be formulated with an aqueous or non-aqueous base also comprising one more more dispersing agents, solubilising agents or suspending agents. Liquid sprays are conveniently delivered from pressurised packs.

For administration by inhalation the compounds according to the invention are conveniently delivered from an insufflator, nebuliser or a pressurised pack or other convenient means of delivering an aerosol spray. Pressurised packs may comprise a suitable propellant such as dichlorodifluoromethane, trichlorofluoromethane, dichlorotetrafluoroethane, carbon dioxide or other suitable gas. In the case of a pressurised aerosol the dosage unit may be determined by providing a valve to deliver a metered amount.

Alternatively, for administration by inhalation or insufflation, the compounds according to the invention may take the form of a dry powder composition, for example a powder mix of the compound and a suitable powder base such as lactose or starch. The powder composition may be presented in unit dosage form in, for example, capsules or cartridges or e.g. gelatin or blister packs from which the powder may be administered with the aid of an inhaler or insufflator.

When desired the above described formulations adapted to give sustained release of the active ingredient may be employed.

The pharmaceutical compositions according to the invention may also contain other active ingredients such as antimicrobial agents, or preservatives.

The compounds of the invention may also be used in combination with other therapeutic agents for example other antiinfective agents. In particular the compounds of the invention may be employed together with known antiviral agents.

The invention thus provides, in a further aspect, a combination comprising the compound (A) or a physiologically acceptable derivative thereof together with another therapeutically active agent, in particular an antiviral agent.

The combinations referred to above may conveniently be presented for use in the form of a pharmaceutical formulation and thus pharmaceutical formulations comprising a combination as defined above together with a pharmaceutically acceptable carrier therefor comprise a further aspect of the invention.

Suitable therapeutic agents for use in such combinations include acyclic nucleosides such as acyclovir or ganciclovir, interferons such as α, β or γ-interferon, renal excretion inhibitors such as probenecid, nucleoside, transport inhibitors such as dipyridamole, 2',3'-dideoxynucleosides such as AZT, 2',3'-dideoxycytidine, 2',3'-dideoxyadenosine, 2',3'-dideoxyinosine, 2',3'-dideoxythymidine, 2',3'-dideoxy- 2',3'-didehydrothymidine and 2',3'-dideoxy-2',3'-didehydrocytidine, immunomodulators such as interleukin II (IL2) and granulocyte macrophage colony stimulating factor (GM-CSF), erythropoetin, empligen, thymomudulin, thymopentin, foscarnet, ribavirin and inhibitors of HIV binding to CD4 receptors e.g. soluble CD4, CD4 fragments, CD4 hybrid molecules, glycosylation inhibitors such as 2-deoxy-D-glucose, castanospermine and 1-deoxynojirimycin.

The individual components of such combinations may be administered either sequentially or simultaneously in separate or combined pharmaceutical formulations.

When the compound (A) or a pharmaceutically acceptable derivative thereof is used in combination with a second therapeutic agent active against the same virus the dose of each compound may be either the same as or differ from that when the compound is used alone. Appropriate doses will be readily appreciated by those skilled in the art.

The compound (A) and its pharmaceutically acceptable derivatives may be prepared by any method known in the art for the preparation of compounds of analogous structure, for example as described in European Patent Application Publication No. 0382562.

It will be appreciated by those skilled in the art that for certain of the methods described herein below the desired stereochemistry of the compound (A) may be obtained either by commencing with an optically pure starting material or by resolving the racemic mixture at any convenient stage in the synthesis. In the case of all the processes the optically pure desired product may be obtained by resolution of the end product of each reaction.

In one such process (A) a 1,3-oxathiolane of formula (VIII)

(VIII)

wherein the anomeric group L is a displaceable group, is reacted with an appropriate base. Suitable groups L include —OR where R is an alkyl group, e.g. a $C_{1-6}$alkyl group such as methyl or R is an acyl group, e.g. a $C_{1-6}$alkyl group such as acetyl or halogen, for example iodine, bromine or chlorine.

The compound of formula VIII is conveniently reacted with cytosine or an appropriate pyrimidine base precursor thereof (previously silylated with a silylating agent such as hexamethyldisilazane) in a compatible solvent such as methylene chloride using a Lewis acid such as titanium tetrachloride, tin (IV) compound such as $SnCl_4$, or trimethylsilyltriflate.

The 1,3-oxathiolanes of formula (VIII) may be prepared for example by reaction of an aldehyde of formula (VII) with a mercaptoacetal of formula (VI) in a compatible organic solvent, such as toluene in the presence of an acid catalyst for example a Lewis acid such as zinc chloride.

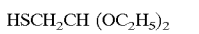 (VI)

 (VII)

The mercaptoacetals of formula (VI) may be prepared by methods known in the art, for example G. Hesse and I. Jorder, *Chem. Ber* 85, 924–932 (1952).

The aldehydes of formula (VII) may be prepared by methods known in the art for example E. G. Halloquist and H. Hibbert, Can. J. Research, 8, 129–136 (1933). Conveniently the crude aldehyde (VII) may be purified by conversion to the crystalline bisulphite addition adduct and subsequent reconversion to the free aldehyde.

In a second process (B) the compound (A) is obtained by base interconversion of a compound of formula (IX)

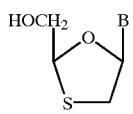 (IX)

where B is a base convertible to cytosine. Such interconversion may be effected either by simple chemical transformation (e.g. the conversion of uracil base to cytosine) or by an enzymatic conversion using a deoxyribosyl transferase. Such methods and conditions for base interconversion are well known in the art of nucleoside chemistry.

In a third process (C) a compound of formula (XI)

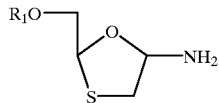 (XI)

may be converted to the compound (A) by conversion of the anomeric $NH_2$ group to the cytosine base by methods well known in the nucleoside chemistry art.

Many of the reactions described hereinabove have been extensively reported in the context of nucleoside synthesis, for example in *Nucleoside Analogs—Chemistry, Biology and Medical Applications*, R. T. Walker et. al., eds, Plenum Press, New York (1979) at pages 165–192; T. Ueda in Chemistry of Nucleosides and Nucleotides, Vol I, L B Townsend ed., Plenum Press, New York (1988) at pages 165–192 the disclosures of which are incorporated by reference herein.

It will be appreciated that the above reactions may require the use of, or conveniently may be applied to, starting materials having protected functional groups, and deprotection might thus be required as an intermediate or final step to yield the desired compound. Protection and deprotection of functional groups may be effected using conventional means. Thus, for example, amino groups may be protected by a group selected from aralkyl (e.g. benzyl), acyl, aryl (e.g. 2,4-dinitrophenyl) or silyl; subsequent removal of the protecting group being effected when desired by hydrolysis or hydrogenolysis as appropriate using standard conditions. Hydroxyl groups may be protected using any conventional hydroxyl protecting group, for example, as described in 'Protective Groups in Organic Chemistry', Ed. J. F. W. McOmie (Plenum Press, 1973) or 'Protective Groups in Organic Synthesis' by Theodora W. Greene (John Wiley and Sons, 1981). Examples of suitable hydroxyl protecting groups include groups selected from alkyl (e.g. methyl, t-butyl or methoxymethyl), aralkyl ( e.g. benzyl, diphenylmethyl or triphenylmethyl), heterocyclic groups such as tetrahydropyranyl, acyl (e.g. acetyl or benzoyl) and silyl groups such as trialkylsilyl (e.g. t-butyldimethylsilyl). The hydroxyl protecting groups may be removed by conventional techniques. Thus, for example, alkyl, silyl, acyl and heterocyclic groups may be removed by solvolysis, e.g. by hydrolysis under acidic or basic conditions. Aralkyl groups such as triphenylmethyl may similarly be removed by solvolysis, e.g. by hydrolysis under acidic conditions. Aralkyl groups such as benzyl may be cleaved for example by treatment with $BF_3$/etherate and acetic anhydride followed by removal of acetate groups so formed at an appropriate stage in the synthesis. Silyl groups may also conveniently be removed using a source of fluoride ions such as tetra-n-butylammonium fluoride.

In the above processes compound (A) is generally obtained as a mixture of the cis and trans isomers of which the cis isomer is the compound of interest.

These isomers may be separated by physical means e.g. chromatography on silica gel or by fractional crystallisation, either directly or on a suitable derivatives thereof, eg acetates (prepared for example with acetic anhydride) followed, after separation, by conversion back to the parent product (eg by deacetylation with methanolic ammonia).

Pharmaceutically acceptable salts of the compounds of the invention may be prepared as described in U.S. Pat. No. 4,383,114, the disclosure of which is incorporated by reference herein. Thus, for example, when it is desired to prepare an acid addition salt of compound (A) the product of any of the above procedures may be converted into a salt by treatment of the resulting free base with a suitable acid using conventional methods. Pharmaceutically acceptable acid addition salts may be prepared by reacting the free base with an appropriate acid optionally in the presence of a suitable solvent such as an ester (e.g. ethyl acetate) or an alcohol (e.g. methanol, ethanol or isopropanol). Inorganic basic salts may be prepared by reacting the parent compound with a suitable base such as an alkoxide (e.g. sodium methoxide) optionally in the presence of a solvent such as an alcohol (e.g. methanol). Pharmaceutically acceptable salts may also be prepared from other salts, including other pharmaceutically acceptable salts, of the compound (A) using conventional methods.

Compound (A) may be converted into a pharmaceutically acceptable phsophate or other ester by reaction with a phosphorylating agent, such as $POCl_3$, or a suitable esterifying agent, such as an acid halide or anhydride, as appropriate. An ester or salt of compound (A) may be converted to the parent compound for example by hydrolysis.

Resolution of the final product, or an intermediate or starting material therefor may be effected by any suitable method known in the art: see for example 'Stereochemistry of Carbon Compounds' by E. L. Eliel (McGraw Hill, 1962) and 'Tables of Resolving Agents' by S. H. Wilen.

Thus for example the compound (A) may obtained by chiral HPLC using suitable stationary phase for example acetylated β-cyclodextrin or cellulose triacetate and suitable solvent for example an alcohol such as ethanol or an aqueous solution of for example triethyl ammonium acetate. Alternatively the compounds may be resolved by enzyme mediated enantioselective catabolism with a suitable enzyme such as cytidine deaminase or selective enzymatic degradation of a suitable derivative using a 5'-nucleotidase. When resolution is effected enzymatically the enzyme may be employed either in solution or, more conveniently, in immobilised form. Enzymes may be immobilised by any method known in the art, for example by adsorption onto a resin such as Eupergit C.

The invention will be further described by the following examples which are not intended to limit the invention in any way. All temperatures are in degrees Celcius.

INTERMEDIATE 1

5-Methoxy-1,3-oxathiolane-2-methanol, benzoate

A solution of zinc chloride (1.6 g) in hot methanol (15 ml) was added to a stirred solution of mercaptoacetaldehyde, dimethyl acetal (34.2 g) and benzoyloxy acetaldehyde (48.3 g) in toluene (1300 ml) which was then heated to reflux under nitrogen for 50 min. The cooled mixture was concentrated, diluted with some toluene, then filtered through Kiesulguhr. The combined filtrates and toluene were washed with aqueous saturated sodium bicarbonate solution (×2) and brine, dried (MgSO$_4$) then evaporated to an oil which was subjected to column chromatography on silica (2 kg, Merck 9385) eluted with chloroform to give the title product as an oil (45.1 g) a mixture of anomers (ca 1:1) 1H NMR (DMSO-d$_6$) 3.1–3.3 (4H), 3.42 (6H), 4.4–4.6 (4H), 5.41 (1H), 5.46 (1H), 5.54 (1H), 5.63 (1H), 7.46 (4H), 7.58 (2H), 8.07 (4H); δmax (CHBr$_3$) 1717.6 cm$^{-1}$.

INTERMEDIATE 2

(±)-cis-1-(2-Benzoyloxymethyl-1,3-oxathiolan-5-yl)-(1H)-pyrimidin-2-4-dione

A mixture of finely ground uracil (9.62 g) hexamethyl disilazane (50 ml) and ammonium sulphate (30 mg) was heated at reflux under nitrogen until a clear solution was obtained. This was cooled and then evaporated to a colourless oil, which was dissolved, under nitrogen atmosphere, in acetonitrile (100 ml). The solution was added to a stirred ice cooled solution of 5-methoxy-1,3-oxathiolane-2-methanol, benzoate (intermediate 1) (19.43 g), in acetonitrile (600 ml) and trimethyl silyl trifluoromethanesulphonate (14.7 ml) was added. The ice bath was removed, and the solution was heated at reflux under nitrogen for 45 mins. After cooling and evaporation, the residue was purified by column chromatography over 1 kg of silica gel (Merck 9385) eluting with chloroform/methanol 9:1. Appropriate fractions were cooled and evaporated to afford a crude residue. This was fractionally crystallized from the minimum of hot methanol (c.1200 ml) to afford the title compound (6.32 g) as white crystals. 1H NMR (d$^6$DMSO) δ 11.36 (1H, bs). 7.50–8.00 (6H, m), 6.20 (1H, t), 5.46 (2H, m), 4.62 (2H, m), 3.48 (1H, m), 3.25 (1H, m).

INTERMEDIATE 3

(±)-(cis)-4-Amino-1-(2-benzoyloxymethyl-1,3-oxathiolan-5-yl)-(1H)-pyrimidin-2-one Method (a)

A suspension of cytosine (20.705 g) and ammonium sulphate (few mgs) in hexamethyldisilazane (110 ml) was stirred and heated at reflux for 2½ h, under nitrogen. Solvent was removed by evaporation, and the residual solid was dissolved in dry acetonitrile (350 ml). This solution was transferred using flexible needle techniques into a stirred, ice-chilled solution of 5-methoxy-1,3-oxathiolane-2-methanol, benzoate (Intermediate I) (43.57 g) in acetonitrile (650 ml) under nitrogen. Trimethylsilyl trifluoromethane-sulphonate (33 ml) was added, the solution was allowed to warm to ambient temperature (1½ h) then heated to reflux for an overnight period. The residue mixture was concentrated, diluted with saturated aqueous sodium bicarbonate solution (500 ml), then extracted with ethyl acetate (3×500 ml). The combined extracts were washed with water (2×250 ml) and brine (250 ml) dried (MgSO$_4$) then evaporated to a foam which was subjected to column chromatography on silica (600 g, merck 7734), eluted with ethyl acetate-methanol mixtures to give a mixture of anomers (ca 1:1 31.59 g). The mixture was crystallized from water (45 ml) and ethanol (9.0 ml) to give a solid (10.23 g) which was recrystallised from ethanol (120 ml) and water (30 ml) to give the title product as a white solid (9.26 g); λmax (MeOH) 229.4 mm (E$^{1\%}$ 610); 272.4 mm (E$^{1\%}$ 293); $^1$H NMR (DMSO d6) δ 3.14 (1H), 3.50 (1H), 4.07 (2H), 5.52 (1H), 5.66 (1H); 6.28 (1H), 7.22 (2H), 7.56 (2H), 7.72 (2H), 8.10 (2H).

Method (b)

Phosphorus oxychloride (7.0 ml) was added dropwise to a stirred, ice-cooled suspension of 1,2,4-triazole (11.65 g) in acetonitrile (120 ml) then, keeping the internal temperature below 15° C. triethylamine (22.7 ml) was added dropwise. After 10 min a solution of (±)-cis-1-(2-benzoyloxymethyl-1,3-oxathiolan-5-yl)-(1H)-pyrimidin-2,4-dione (Intermediate 2) (6.27 g) in acetonitrile (330 ml) was slowly added. Stirring was then continued at room temperature overnight. The mixture was cooled by means of an ice bath and triethylamine (30 ml) was slowly added followed by water (21 ml). The resultant solution was evaporated, and the residue was partitioned between saturated sodium bicarbonate solution (400 ml) and chloroform (3×200 ml). The combined chloroform extracts were dried and magnesium sulphate, filtered and evaporated to give a crude residue (9.7 g). The residue was dissolved in 1,4-dioxan (240 ml) and concentrated aqueous ammonia solution (s.g 0.880, 50 ml) was added. After 1½ h the solution was evaporated and the residue dissolved in methanol. This caused precipitation of a solid, which was filtered off. The mother liquors were purified by column chromatography over silica gel (Merck 9385, 600 g). Appropriate fractions were pooled and evaporated to give the title compound as a fawn solid (2.18 g), identical to that obtained by Method (a).

EXAMPLE 1

(±)-(cis)-4-Amino-1-(2-hydroxymethyl-1,3-oxathiolan-5-yl)-(1H)-pyrimidin-2-one

A suspension of (cis)-4-1-(2-benzoyloxymethyl-1,3-oxathiolan-5-yl)-(1H)-pyrimidin-2-one (Intermediate 3) (8.19 g) and Amberlite IRA-400 (OH) resin (8.24 g) in methanol (250 ml) was stirred and heated to reflux for 1½ h. Solids were removed by filtration then washed with methanol. The combined filtrates were evaporated. The residue was triturated with ethyl acetate (80 ml). The resulting white solid was collected by filtration to give the title product (5.09 g), 1H, NMR (DMSO-d$_6$) 3.04 (1H), 3.40 (1H), 3.73 (2H), 5.18 (1H), 5.29 (1H), 5.73 (1H), 6.21 (1H), 7.19 (2H), 7,81 (1H).

EXAMPLE 2

Chiral HPLC separation of the enantiomers of (±)-(cis)-4-Amino-2-(2-hydroxymethyl-1,3-oxathiolan-5-yl)-(1H)-pyrimidin-2-one (a) The racemic product of Example 1 (25 mg) was subjected to preparative HPLC under the following conditions:

| | |
|---|---|
| Column: | Merck Hibar cellulose triacetate, 250 × 10 mm, 10µ |
| Eluant: | ethanol; |
| Flow: | 3 ml/min; |
| Detection: | uv, 270 nm; |
| Temperature: | ambient. |

Evaporation of the appropriate pooled fractions gave (2R, cis)-4-amino-1-(2-hydroxymethyl-1,3-oxathiolan-5-yl)-(1H)-pyrimidin-2-one (6.8 mg, e.e. ca 100%) and (2S,cis)-4-amino-1-(2-hydroxymethyl-1,3-oxathiolan-5yl)-(1H)-pyrimidin-2-one (3.6 mg, e.e. ca 90%).

(B) The racemic product of Example 1 (26 mg) was subjected to preparative HPLC under the following conditions:

Column: ASTEC cyclobond I acetyl, 250×4.6 mm;
Eluant: 0.2% triethylammonium acetate (prepared by adding glacial acetic acid to 0.2% triethylamine in water, to a final pH 7.2);

| Flow: | 2 ml/min; |
|---|---|
| Detection: | uv, 300 nm; |
| Temperature: | ambient. |

Evaporation of appropriate fractions gave crude (2R,cis)-4-amino-1-(2-hydroxymethyl-1,3-oxathiolan-5-yl)-(1H)-pyrimidin-2-one (25 mg) and crude (2S,cis)-4-amino-1,2-(2-hydroxymethyl-1,3-oxathiolan-5-yl)-(1H)-pyrimidin-2-one (17 mg). These fractions were separately subjected to further preparative HPLC run under the following conditions:

| Column: | ASTEC cyclobond I acetyl, 250 × 4.6 mm |
|---|---|
| Eluent: | 15 mM ammonium acetate,, pH 6.8; |
| Flow: | 0.5 ml/min |
| Detection: | uv, 300 nm; |
| Temperature: | 5°. |

Evaporation of the appropriate pooled fractions gave (2R, Cis)-4-amino-1-(2-hydroxymethyl-1,3-oxathiolan-5-yl)-(1H)-pyrimidin-2-one (5.0 mg, e.e. ca 91%) and (2S, cis)-4-amino-1-(2-hydroxymethyl-1,3-oxathiolan-5-yl)-(1H)-pyrimidin-2-one (7.6 mg, e.e ca 96%).

EXAMPLE 3
(−)-cis-4-Amino-1-(2-hydroxymethyl-1,3-oxathiolan-5-yl)-(1H)-pyrimidin-2-one (ii) (±)-cis-4-Amino-1-(2-hydroxymethyl-1,3-oxathiolan-5-yl)-(1H)-pyrimidinone, dihydrogenophosphate, ammonium salt A cold (0°), stirred suspension of (±)-cis-4-amino-1-(2-hydroxymethyl-1,3-oxathiolan-5-yl)-(1H)-pyrimidin-2-one (1.00 g) (Example 1) in dry trimethylphosphate (20 ml) was treated with phosphorous oxychloride (2.44 ml), and the mixture was stirred at 0° for 35 mins then quenched in ice water (60 g). The cold mixture was adjusted to pH 2.5 by the addition of aqueous N-sodium hydroxide, then applied to a charcoal column (10 g, DARCO), which was eluted with water, then ethanol-aqueous ammonia. Fractions containing crude monophosphate were combined and concentrated. The resulting solution was applied to a column containing 25 g of DEAE Sephadex A-25 ($HCO_3$-form). Elution was performed with a gradient of water (120 ml) to 0.1M-$NH_4HCO_3$ (240 ml), then 0.2, 0.3 and 4M $NH_4HCO_3$ (120, 240, 400 ml respectively). Appropriate fractions were combined and concentrated. The residual solution was diluted with water (40 ml) and freeze-dried to give the title product as a white solid (1.37 g); λmax (pH6 buffer), 271.0 nm ($E^{1\%}_{1cm}$ 190); $^1$H NMR (D20) δ3.23 (1H), 3.55 (1H), 4.0-4.2 (2H), 5.43 (1H), 6.07 (1H), 6.33 (1H), 8.08 (1H).

(ii) (2R, cis)-4-Amino-1-(2-hydroxymethyl-1,3-oxathiolan-5yl)-(1H)-pyrimidin-2-one and (2S,cis)-4-Amino-1-(2-hydroxymethyl-1-3-oxathiolan-5-yl)-(1H)-pyrimidin-2-one 5′-Nucleotidase (from crotalus atrox venom) [EC 3.1.3.5] (60 mg at 17 units/mg) was added to a solution of (±)-cis-4-amino-(2-hydroxymethyl-1,3-oxathiolan-5-yl)-(1H)-pyrimidin-2-one, 6′-dihydrogenphosphate, ammonium salt (1.35 g) in buffer [30 ml, prepared from glycine (526 mg) and magnesium chloride (190 mg) in water (100 ml)] and the mixture was incubated at 37° for 2.5 h. More enzyme (20 mg) was added, and incubation was continued for a further 3.5 h. The resulting mixture was applied to a column of DEAE Sephadex A-25 ($HCO_3$-form). Elution was performed with water (160 ml), then 0.1, 0.2, 0.3 and 0.4M $NH_4HCO_3$ (200 ml) each). Appropriate fractions containing the first eluted component were combined and evaporated, the residue was subjected to column chromatography on silica (60 g, Merck 7734), eluted with chloroform-methanol mixtures. Evaporation of the appropriate fractions from methanol-ethyl acetate gave (2R, Cis)-4-amino-1-(2-hydroxymethyl-1,3-oxathiolan-5-yl)-(1H)-pyrimidin-2-one as a white solid (0.30 g)- $[\alpha]D^{21}+137°$ (c.1.04 MeOH); $^1$H NMR (DMSO) δ 3.04 (1H), 3.40 (1H), 3.73 (2H), 5.18 (1H), 5.29 (1H), 5.73 (1H), 6.21 (1H), 7.19 (2H), 7.81 (1H).

Appropriate fractions from the Sephadex column, containing the second eluted component, were combined and evaporated. The residue was dissolved in water (30 ml), treated with alkaline phosphatase (from *Escherichia coli*) [EC 3.1.3.1] (1.5 ml at 416 units/ml), then incubated at 37° for one hour. Solvent was removed by evaporation and the residue was subjected to column chromatography on silica (60 g, Merck 7734), eluted with chloroform-methanol mixtures. Evaporation of the appropriate fractions from methanol-ethyl acetate gave (2S,cis)-4-amino-1-(2-hydroxymethyl-1,3-oxathiolan-5-yl)-(1H)-pyrimidin-2-one as a white solid (0.32 g); $[\alpha]D^{21}-132°$ (c. 1.08, MeOH); $^1$H NMR (DMSO) δ 3.04 (1H),3.40 (1H), 3.73 (2H), 5.18 (1H), 5.29 (1H); 5.73 (1H), 6.21 (1H), 7.19 (2H), 7.81 (1H).

EXAMPLE 4
(−)-cis-4-Amino-1-(2-hydroxymethyl-1,3-oxathiolan-5-yl)-(1H) pyrimidin-2-one (i) Three 50 ml flasks of nutrient broth (Oxoid Ltd) were innoculated with a loopful each of *Escherichia coli* (ATCC 23848) scraped from a Nutrient Agar plate. The flasks were incubated overnight at 37° C. with shaking at 250 rev/min and then each flask was used to innoculate 4l of CDD medium (glutamic acid, 3 g/l; $MgSO_4$, 0.2 g/l; $K_2SO_4$, 2.5 g/l; NaCl, 2.3 g/l; $Na_2HPO_4 2H_2O$, 1.1 g/l, $NaH_2PO_4 2H_2$) 0.6 g/l cytidine, 1.2 g/l) in a seven liter fermenter. The cultures were fermented at 750 rev/min, 37° C. with aeration at 4l/min. After growth for 24 hrs the cells were collected by centrifugation (5000 g, 30 minutes) to yield 72 g wet weight. The cell pellet was resuspended in 300 ml of 20 mM Tris HCl buffer (pH 7.5) and disrupted by sonication (4×45 seconds). The cell debris was removed by centrifugation (30,000 g, 30 minutes) and the protein in the supernatant was precipitated by addition of ammonium sulphate to 75% saturation. The precipitate was collected by centrifugation (30,000 g. 30 minutes) and the pellet was resuspended in 25 ml of HEPES buffer (100 mM, pH 7.0) containing ammonium sulphate (75% saturation). Enzyme solution was prepared by centrifugation at 12,000 rpm for 30 mins. The supernatant was discarded and the pellet dissolved in Tris HCl buffer (pH 7.0; 10 mM) to the original volume.

(ii) The product of Example 1 (115 mg was dissolved in water (100 ml), and stirred. Enzyme solution (0.5 ml) was added, and the mixture was maintained at a constant pH by the continual addition of CHl (25 mM). The conversion was monitored by chiral HPLC, which showed that the (−) enantiomer of the substrate was preferentially deaminated. After 22 hr the (+) enantiomer of the substrate (RT 12.5 min) had been completely removed, and the solution was adjusted to pH 10.5 by the addition of conc. sodium hydroxide.

The solution produced above was eluted through a column of QAE Sephadex (A25; Pharmacia; 30×1.6 cm), pre-equilibrated to pH11. The column was washed with water (22 ml) and then with HCl (0.1M). Fractions (40 ml) were taken, and analysed by reversed phase HPLC. Fractions 5–13, containing the unreacted (−) enantiomer of the substrate, were combined and adjusted to pH 7.5 with HCl. Fraction 47, containing deaminated product, was adjusted to pH7.5 with dil. NaOH. Analysis by chiral HPLC showed that this material was a mixture, consisting of one enantiomer (RT 10.2 min) as the major component with the other enantiomer (RT 8.5 min) as a minor component (e.e ca 90%).

(iii) Stage (ii) above was repeated on a larger scale. The compound of Example 1 (363 mg) in 250 ml of water was incubated with enzyme solution (0.5 ml), prepared as in Stage (i). Further aliquots (0.5 ml) of enzyme were added after 18 and 47 hrs. The reaction mixture was stirred for 70 h., then left standing for a further 64 h. analysis by chiral hplc indicated that the (+) enantiomer of the substrate had been completely deaminated, and the resulting solution was adjusted to pH10.5 with NaOH.

The solution above was loaded onto the same QAE column, and eluted as in stage (i). Fractions 2–6, containing a mixture of the residual substrate and deaminated product, were bulked. Fractions 7–13, containing the residual substrate (−) enantiomer), were bulked and adjusted to pH7.5. Fractions 25–26, containing deaminated product, were bulked and neutralised.

Fractions 2–6 above were re-eluted through the same QAE column. Fractions 3–11 from this second column contained unreacted substrate ((−) enantiomer). Fraction 70 contained the deaminated product.

(iv) The resolved substrate fractions from stage (II) and (iii) were combined and adjusted to pH7.5. This solution was eluted through a column of XAD-16 (40×2.4 cm), packed in water. The column was washed with water, and then eluted with acetone:water (1:4 v/v). Fractions containing the (−) enantiomer of BCH 189 were bulked and freeze-dried to give a white powder (190 mg).

The HPLC methods used above were as follows:

1. Reversed Phase analytical HPLC

| Column: | Capital Cartridge |
| | Spherisorb ODS-2 (5 uM) |
| | 150 × 4.6 mm |
| Eluant: | Ammonium dihydrogen phosphate (50 mM) + 5% MeCN |
| Flow: | 1.5 ml/min |
| Detection: | UV, 270 nm |
| Retention Times: | BCH 189 5.5 min |
| | deaminated BCH -189 8.1 min |

2. Chiral analytical HPLC

| Column: | Cyclobond I Acetyl |
| | 250 × 4.6 mm |
| Eluant: | 0.2% Triethylammonium acetate (pH 7.2) |
| Flow: | 1.0 ml/min |
| Detection: | UV, 270 nm |
| Retention Times: | BCH 189 11.0 and 12.5 min |
| | deaminated BCH-189 8.5 and 10.2 min |

(The bioconversion was followed by monitoring the loss of the peak at 12.5 min., and accumulated of product at 10.2 min).

EXAMPLE 5

(−)-cis-4-Amino-1-(2-hydroxymethyl-1,3-oxathiolan-5-yl)-(1H)-pyrimidin-2-one

A loopful of *E. coli* B cells (ATCC 32848) scraped from a well grown nutrient agar plate was used to inoculate two Florence flasks each containing 250 ml of nutrient broth. The culture was incubated at 37° with shaking (250 rev/min, 5 cm throw) for 18 hours. This was then used to inoculate 40 L of CDD-medium, with cytidine, in a 70 L fermenter.

Conditions for the fermentation were as follows: 40 L/min aeration, 750 rev/min stirring speed at a temperature of 37° C. Three Rushton impellers were fitted to the fermenter. The fermentation was run for 18 hours before harvest using a Sharples continuous centrifuge. The cell paste (150 g net weight) was frozen at −20° C. prior to cell breakage.

| CDD Medium | |
|---|---|
| | g/L |
| L-Glutamic acid | 3 |
| $MgSO_4$ | 0.2 |
| $K_2SO_4$ | 2.5 |
| NaCl | 2.3 |
| $Na_2HPO_4$ | 1.1 |
| $NaH_2PO_4$ | 0.6 |

Made with distilled water. Sterilised at 121° C. for 30 minutes. Cytidine (1.2 g/L) was filter sterilised and added prior to inoculation.

The frozen cell paste (150 g) was thawed and suspended in 750 ml of 100 mM Hepes (N-[2-hydroxyethyl]piperazine-N'-[2-ethane sulphonic acid]) buffer (pH 7.5) containing 1 mM ethylenediaminetetraacetic acid (sodium salt) and 1 mM dithiothreitol (disruption buffer). The cells were disrupted by passing the suspension through a Manton-Gaulin homogeniser operating at 7500 psi. This was carried out three times with cooling of the suspension to approximately 5° C. after each pass through the homogeniser. The homogenate was clarified by centrifugation (1400 g; 60 min). The cytidine deaminease activity was adsorbed onto a Q-Sepharose column (490 mg bed volume) pre-equilibrated with 50 mM Tris (hydroxymethyl) methylamine (pH 7.5) containing 1 mM sodium chloride. The pooled active fractions (210 ml) were added onto a phenyl-Sepharose column (490 ml) bed volume), pre-equilibrated with the sample buffer containing 3.2M ammonium sulphate. The bound enzyme was eluted by a gradient of decreasing ammonium sulphate concentration. Fractions containing the cytidine deaminase activity were pooled (695 ml) and the partially purified enzyme was then precipitated with 80% ammonium sulphate. After centrifugation (1400 g; 60 min) the pellet was resuspended in 54 ml of supernatant from the above and stored at 4° C.

6.2 ml of this solution was centrifuged (18000 g, 90 min) and the pellet was dissolved in 24 ml of 0.5M potassium phosphate buffer (pH 7.5). The suspension was dialysed overnight against 1M potassium phosphate buffer (pH 7.5). The retentate (20 ml) was then diluted with an equal volume of distilled water. To 35 ml of this solution dry Eupergit C beads were added (1 g) and the mixture was allowed to stand at room temperature 150–300 hours (determined by measuring residual cytidine deaminase activity in solution). The immobilised enzyme was washed with 100 mM Tris.HCl buffer (pH 7.0) containing 1 mM EDTA, 1 mM DTT, 0.5M NaCl and 500 ppm p-hydroxybenzoic acid ethyl ester (storage buffer). The immobilised enzyme (2.7 g wet weight) was stored in this buffer at 4° C. until required for biotransformation.

The product of Example 1 (3 g) was dissolved in 500 ml of distilled water in a magnetically stirred 1 L flask. The bioconversion was carried out at 32° C. in a pH-stat. The pH was maintained constant at 7.0 by addition of 1M acetic acid. 1 g Wet weight of the immobilised enzyme beads was washed with distilled water prior to start of the reaction. The conversion was monitored by chiral-HPLC which showed that the (+) enantiomer of the substrate was preferentially deaminated. At the end of the reaction (72 h) the enzyme beads were filtered off and the filtrate was used for isolation of the desired (−)-enantiomer.

The pH of the reaction mixture was adjusted to pH 10.5 using ammonia solution (1M) and the solution applied to Duolite A113 super resin in the OH cycle (50 ml; 0.4 bed volumes per hour). The uridine analogue adsorbed to the resin and the (−)-enantiomer passed straight through. Any (−)-enantiomer still on the resin was removed by washing with 0.04% ammonia solution (2 bed volumes; flow rate 0.8 bed volumes/hour).

The pH of the spent solutions and washes (600 ml) was adjusted to pH 7.0 with concentrated sulphuric acid and the solution applied to XAD16 resin (50 ml; flow rate 1.4 bed volumes per hour). The column was washed with distilled water (2.5 bed volumes, flow rate 2 bed volumes per hour) and the (−)-enantiomer eluted with acetone:water 1:3 (flow rate 1.5 bed volumes per hour).

The bulk (−)-enantiomer containing fraction (4 bed volumes) was concentrated on a Buchi evaporator to a small volume before filtration through a No. 3 glass sinter. The filtered solution was freeze dried to yield 1.2 g of title product identical to that obtained in Example 4.

EXAMPLE 6

Tablet Formulations

A. The following formulation is prepared by wet granulation of the ingredients with a solution of providone in water, drying and screening, followed by addition of magnesium stearate and compression.

|   |   |   | mg/tablet |
|---|---|---|---|
| (a) | Active ingredient | | 250 |
| (b) | Lactose B.P. | | 210 |
| (c) | Providone B.P. | | 15 |
| (d) | Sodium Starch Glycollate | | 20 |
| (e) | Magnesium Stearate | | 5 |
|   |   |   | 500 |

B. The following formulation is prepared by direct compression; the lactose is of the direct compression type.

|   | mg/tablet |
|---|---|
| Active Ingredient | 250 |
| Lactose | 145 |
| Avicel | 100 |
| Magnesium Stearate | 5 |
|   | 500 |

C. (Controlled Release Formulation). The formulation is prepared by wet granulation of the ingredients (below) with a solution of providone in water, drying and screening followed by the addition of magnesium stearate and compression.

|   |   |   | mg/tablet |
|---|---|---|---|
| (a) | Active ingredient | | 500 |
| (b) | Hydroxypropylemethylcellulose (Methocel K4M Premium) | | 112 |
| (c) | Lactose B.P. | | 53 |
| (d) | Providone B.P. | | 28 |
| (e) | Magnesium Stearate | | 7 |
|   |   |   | 700 |

EXAMPLE 7

Capsule Formulation

A capsule formulation is prepared by admixing the ingredients below and filling into a two-part hard gelatin capsule.

|   | mg/capsule |
|---|---|
| Active ingredient | 125 |
| Lactose | 72.5 |
| Avicel | 50 |
| Magnesium Stearate | 2.5 |
|   | 250 |

EXAMPLE 8

Injectable formulation

Active ingredient 0.200 g

Sodium hydroxide solution, 0.1M q.s. to a pH of about 11.

Sterile water q.s. to 10 ml

The active ingredient is suspended in some of the water (which may be warmed) and the pH adjusted to about 11 with a solution of sodium hydroxide. The batch is then made up to volume and filtered through a sterilizing grade membrane filter into a sterile 10 ml glass vial and sealed with sterile closures and overseals.

EXAMPLE 9

|   | mg/suppository |
|---|---|
| Active ingredient | 250 |
| Hard Fat, B.P. | 1770 |
|   | 2020 |

One-fifth of the hard fat is melted in a steam-jacketed pan at 45° C. maximum. The active ingredient is sifted through a 200 μm sieve and added to the molten base with mixing, using a high snear stirrer, until a smooth dispersion is achieved. Maintaining the mixture at 45° C., the remaining hard fat is added to the suspension and stirred to ensure a homogenous mix. The entire suspension is passed through a 250 μm stainless steel screen and, with continuous stirring, is allowed to cool to 40° C. At a temperature of 38° C. to 40° C., 2.02 g of the mixture is filled into suitable, 2 ml plastic molds. The suppositories are allowed to cool to room temperature.

EXAMPLE 10

Biological Activity

Antiviral Activity

Antiviral activity of the compounds of Example 2 were determined against three strains of HIV-1 and one strain of HIV-2 in the follow cell lines.

JM cells, a semi-mature T-cell line derived from a patient with lymphoblastic leukaemia, infected with HIV-1 strain GB8.

C8166 cells, a human T-lymphoblastoid cell line, infected with HIV-1 strain RF.

MT-4 cells, a human T-cell leukaemia cell line, infected with HIV-1 strain RF.

CEM cells, a human T-lymphoblastoid cell line, infected with HIV-1 strains RF and U455, or HIV-2 strain ROD.

Antiviral activities in C8166, JM, and CEM cells were determined by inhibition of syncytium formation (Tochikura et al Virology, 164, 542–546) and in MT-4 cells by inhibition of formazan conversion (Baba et al; (1987) Biochem Biophys Res Commun., 142, 128–134; Mossman (1983) J. Immun Meth; 65, 55–57). Antiviral activities were also determined by analysing the amount of HIV p24 antigen synthesised in the presence and absence of enantiomers.

The results are shown in Tables 1 and 2 below:

TABLE 1

| | 50% Antiviral Activity ($\mu$g/ml) | | | | | |
|---|---|---|---|---|---|---|
| Assay | Formazan | inhibition of syncytium formation | | | | |
| Cells | MT-4 | CEM | CEM | CEM | JM | C8166 |
| Virus (HIV-1) | HIV-1 RF | HIV-2 ROD | HIV-1 RF | HIV-1 U455 | HIV-1 GB8 | HIV-1 RF |
| (+)-enantiomer | 0.28 | 0.045 | 0.07 | 0.006 | 0.03 | 0.05 |
| (−)-enantiomer | 0.20 | 0.055 | 0.04 | 0.008 | 0.05 | 0.01 |

TABLE 2

Inhibition of HIV p24 Synthesis
50% Inhibition HIV p24 Synthesis ($\mu$g/ml)

| Cells | C8166 | JM | MT-4 |
|---|---|---|---|
| Virus | RF | GB8 | RF |
| (+)-enantiomer | 0.021 | 0.033 | 0.0008 |
| (−)-enantiomer | 0.016 | 0.016 | 0.0004 |

B. Cytotoxicity

The cytotoxicites of the compounds of Example 2, the racemic compound (BCH-189; Example 1) and a 50/50 mixture of the two enantiomers were determined in five CD4 cell lines: H9, JM, CEM, C8166 and U937.

Compounds for test were serially diluted from 100 $\mu$g/ml to 0.3 $\mu$g/ml (final concentrations) in 96 well microtitre plates. $3.6 \times 10^4$ cells were inoculated into each well of the plates including drug-free controls. After incubation at 37° C. for 5 days, the viable cell count was determined by removing a sample of cell suspension and counting trypan blue excluding cells in a haemocytometer.

The results are shown in Table 3.

TABLE 3

| | Cytotoxicity | | | | |
|---|---|---|---|---|---|
| | 50% Cytoxicity ($\mu$g/ml) | | | | |
| Compound | CEM cells | JM cells | H9 cells | U937 cells | C8166 cells |
| (+)-enantiomer | 1 | 1.5 | 2 | 4 | 35 |
| (−)-enantiomer | >100 | 30 | >100 | >100 | >100 |
| BCH-189 | 3 | 3.5 | 8 | 15 | 90 |
| 1:1 Mix of | 2.5 | ND* | ND | ND | ND |

ND = Not Determined

What is claimed is:

1. A method for treating a human suffering from HIV infection comprising administering to said human a pharmaceutical composition comprising: a compound which is (−)-cis-4-amino-1-(2-hydroxymethyl-1,3-oxathiolan-5yl)-(1H)-pyrimidin-2-one or a pharmaceutically acceptable salt thereof, another agent having antiviral activity, and a pharmaceutically acceptable carrier, and wherein the amount of the (+)-enantiomer of said compound or of said pharmaceutically acceptable salt present in said composition is no more than 5% w/w, relative to the combined weight of the (−) and (+)-enantiomers thereof.

2. A method according to claim 1, wherein said agent is an acyclic nucleoside, an interferon, a renal excretion inhibitor, a nucleoside transport inhibitor, a 2',3'-dideoxynucleoside, an immunomodulator, erythropoietin, ampligen, thyomodulin, thymopentin, foscarnet, ribavirin, or an inhibitor of HIV binding to CD4.

3. A method according to claim 1, wherein the amount of said compound or pharmaceutically acceptable salt is 10–1500 mg.

4. A method according to claim 3, wherein the amount of said compound or pharmaceutically acceptable salt is 20–1000 mg.

5. A method according to claim 4, wherein the amount of said compound or pharmaceutically acceptable salt is 50–70 mg.

6. A method according to claim 1, wherein said composition contains an amount of the (+)-enantiomer of no more than 2% w/w.

7. A method according to claim 6, wherein said composition contains an amount of the (+)-enantiomer of no more than 1% w/w.

8. A method according to claim 1, wherein said compound or pharmaceutically acceptable salt and said agent are administered sequentially.

9. A method according to claim 1, wherein said compound or pharmaceutically acceptable salt and said agent are administered simultaneously.

10. A method according to claim 1,
wherein said compound is administered at a dosage of 0.1–750 mg/kg of body weight per day.

11. A method according to claim 10, wherein said compound or pharmaceutically acceptable salt is administered at a dosage of 0.5–60 mg/kg of body weight per day.

12. A method according to claim 11, wherein said compound or pharmaceutically acceptable salt is administered at a dosage of 1–20 mg/kg of body weight per day.

13. A pharmaceutical composition comprising:
a pharmaceutically acceptable carrier, a compound which is (−)-cis-4-amino-1-(2-hydroxymethyl-1,3-oxathiolan-5-yl)-(1H)-pyrimidin-2-one or a pharmaceutically acceptable salt thereof, and another agent having antiviral activity wherein the amount of the (+)-enantiomer of said compound or of said pharmaceutically acceptable salt present in said composition is no more than 5% w/w, relative to the combined weight of the (−) and (+)-enantiomers thereof.

14. A composition according to claim 13, wherein said agent is an acyclic nucleoside, an interferon, a renal excretion inhibitor, a nucleoside transport inhibitor, a 2′,3′-dideoxynucleoside, an immunomodulator, erythropoetin, ampligen, thyomodulin, thymopentin, foscarnet, ribavirin, or an inhibitor of HIV binding to CD4.

15. A composition according to claim 13, wherein said composition contains 10–1500 mg of said compound or pharmaceutically acceptable salt.

16. A composition according to claim 15, wherein said composition contains 20–1000 mg of said compound or pharmaceutically acceptable salt.

17. A composition according to claim 16, wherein said composition contains 50–700 mg of said compound or pharmaceutically acceptable salt.

18. A composition according to claim 13, wherein said compound is (−)-cis-4-amino-1-(2-hydroxymethyl-1,3-oxathiolan-5-yl)-(1H)-pyrimidin-2-one.

19. A composition according to claim 18, wherein said agent is an acyclic nucleoside, an interferon, a renal excretion inhibitor, a nucleoside transport inhibitor, a 2′,3′-dideoxynucleoside, an immunomodulator, erythropoetin, ampligen, thyomodulin, thymopentin, foscarnet, ribavirin, or an inhibitor of HIV binding to CD4.

20. A composition according to claim 18, wherein said composition contains 10–1500 mg of said compound.

21. A composition according to claim 20, wherein said composition contains 20–1000 mg of said compound.

22. A composition according to claim 21, wherein said composition contains 50–700 mg of said compound.

23. A composition according to claim 13, wherein said composition contains an amount of the (+)-enantiomer of no more than 2% w/w.

24. A composition according to claim 23, wherein said composition contains an amount of the (+)-enantiomer of no more than 1% w/w.

25. A composition according to claim 18, wherein said composition contains an amount of the (+)-enantiomer of no more than 2% w/w.

26. A composition according to claim 25, wherein said composition contains an amount of the (+)-enantiomer of no more than 1% w/w.

27. A method according to claim 1, wherein said compound is (−)-cis-4-amino-1-(2-hydroxymethyl-1,3-oxathiolan-5-yl)-(1H)-pyrimidin-2-one.

28. A method according to claim 2, wherein said compound is (−)-cis-4-amino-1-(2-hydroxymethyl-1,3-oxathiolan-5-yl)-(1H)-pyrimidin-2-one.

29. A method according to claim 28, wherein the amount of said compound is 10–1500 mg.

30. A method according to claim 29, wherein the amount of said compound is 20–1000 mg.

31. A method according to claim 30, wherein the amount of said compound is 50–700 mg.

32. A method according to claim 28, wherein said composition contains an amount of the (+)-enantiomer of no more than 2% w/w.

33. A method according to claim 32, wherein said composition contains an amount of the (+)-enantiomer of no more than 1% w/w.

34. A method according to claim 27, wherein said composition contains an amount of the (+)-enantiomer of no more than 2% w/w.

35. A method according to claim 34, wherein said composition contains an amount of the (+)-enantiomer of no more than 1% w/w.

36. A method according to claim 28, wherein said compound and said agent are administered sequentially.

37. A method according to claim 28, wherein said compound and said agent are administered sequentially.

38. A method according to claim 28, wherein said compound is administered at a dosage of 0.1–750 mg/kg of body weight per day.

39. A method according to claim 38, wherein said compound is administered at a dosage of 0.5–60 mg/kg of body weight per day.

40. A method according to claim 38, wherein said compound is administered at a dosage of 1–20 mg/kg of body weight per day.

41. A composition according to claim 19, wherein said composition contains 10–1500 mg of said compound or pharmaceutically acceptable salt.

42. A composition according to claim 41, wherein said composition contains 20–1000 mg of said compound or pharmaceutically acceptable salt.

43. A composition according to claim 42, wherein said composition contains 50–700 mg of said compound or pharmaceutically acceptable salt.

44. A composition according to claim 41, wherein said composition contains an amount of the (+)-enantiomer of no more than 2% w/w.

45. A composition according to claim 44, wherein said composition contains an amount of the (+)-enantiomer of no more than 1% w/w.

46. A method according to claim 1, wherein said compound or pharmaceutically acceptable salt and said agent are administered in combination.

47. A method according to claim 2, wherein said compound or pharmaceutically acceptable and said agent are administered in combination.

48. A method according to claim 28, wherein said compound and said agent are administered in combination.

49. A method for treating a human suffering from HIV infection comprising administering to said human a pharmaceutical composition comprising: a compound which is (−)-cis-4-amino-1-(2-hydroxymethyl-1,3-oxathiolan-5-yl)-1H)-pyrimidin-2-one or a pharmaceutically acceptable salt thereof, and another agent having antiviral activity, wherein the amount of the (+)-enantiomer of said compound or of said pharmaceutically acceptable salt present in said composition is not more than 5% w/w, relative to the combined weight of the (−) and (+)-enantiomers thereof.

50. A method according to claim 49, wherein said composition contains (−)-cis-4-amino-1-(2-hydroxymethyl-1,3-oxathiolan-5-yl)-(1H)-pyrimidin-2-one.

51. A method according to claim 49, wherein said agent is an acyclic nucleoside, an interferon, a renal excretion inhibitor, a nucleoside transport inhibitor, a 2′,3′-dideoxynucleoside, an immunomodulator, erythropoetin, ampligen, thyomodulin, thymopentin, foscarnet, ribavirin, or an inhibitor of HIV binding to CD4.

52. A method according to claim 50, wherein said agent is an acyclic nucleoside, an interferon, a renal excretion inhibitor, a nucleoside transport inhibitor, a 2′,3′-dideoxynucleoside, an immunomodulator, erythropoetin, ampligen, thyomodulin, thymopentin, foscarnet, ribavirin, or an inhibitor of HIV binding to CD4.

53. A pharmaceutical composition comprising:
   a compound which is (−)-cis-4-amino-1-(2-hydroxymethyl-1,3-oxathiolan-5-yl)-(1H)-pyrimidin-2-one or a pharmaceutically acceptable salt thereof, and another agent having antiviral activity
   wherein the amount of the (+)-enantiomer of said compound or of said pharmaceutically acceptable salt present in said composition is no more than 5% w/w, relative to the combined weight of the (−) and (+)-enantiomers thereof.

54. A composition according to claim 53, wherein said composition contains (−)-cis-4-amino-1-(2-hydroxymethyl-1,3-oxathiolan-5-yl)-(1H)-pyrimidin-2-one.

55. A composition according to claim 53, wherein said agent is an acyclic nucleoside, an interferon, a renal excretion inhibitor, a nucleoside transport inhibitor, a 2',3'-dideoxynucleoside, an immunomodulator, erythropoietin, ampligen, thyomodulin, thymopentin, foscarnet, ribavirin, or an inhibitor of HIV binding to CD4.

56. A composition according to claim 54, wherein said agent is an acyclic nucleoside, an interferon, a renal excretion inhibitor, a nucleoside transport inhibitor, a 2',3'-dideoxynucleoside, an immunomodulator, erythropoietin, ampligen, thyomodulin, thymopentin, foscarnet, ribavirin, or an inhibitor of HIV binding to CD4.

57. A combination comprising:
   a compound which is (−)-cis-4-amino-1-(2-hydroxymethyl-1,3-oxathiolan-5-yl)-(1H)-pyrimidin-2-one or a pharmaceutically accepted salt thereof, and another agent having antiviral activity
   wherein the amount of the (+)-enantiomer of said compound or of said pharmaceutically acceptable salt present in said combination is no more than 5% w/w, relative to the combined weight of the (−) and (+)-enantiomers thereof.

58. A combination accroding to claim 57, wherein said combination contains (−)-cis-4-amino-1-(2-hydroxymethyl-1,3-oxathiolan-5-yl)-(1H)-pyrimidin-2-one.

59. A combination according to claim 57, wherein said agent is an acyclic nucleoside, an interferon, a renal extretion inhibitor, a nucleoside transport inhibitor, a 2',3'-dideoxynucleoside, an immunomodulator, erythropoietin, ampligen, thyomodulin, thymopentin, foscarnet, ribavirin, or an inhibitor of HIV binding to CD4.

60. A combination according to claim 58, wherein said agent is an acyclic nucleoside, an interferon, a renal excretion inhibitor, a nucleoside transport inhibitor, a 2',3'-dideoxynucleoside, an immunomodulator, erythropoietin, ampligen, thyomodulin, thymopentin, foscarnet, ribavirin, or an inhibitor of HIV binding to CD4.

61. An article of manufacture according to claim 61, wherein said first amount contains (−)-cis-4-amino-1-(2-hydroxymethyl-1,3-oxathiolan-5-yl)-(1H)-pyrimidin-2-one or a pharmaceutically acceptable salt thereof, wherein the content of the (+)-enantiomer of said compound or of said pharmaceutically acceptable salt present in said fist amount is no more than 5% w/w/, relative to the combined weight of the (−) and (+)-enantiomers thereof, and
   a second amount of another agent having antiviral activity.

62. An article of manufacture according to claim 61, wherein said first amount contains (−)-cis-4-amino-1-(2-hydroxymethyl-1,3-oxathiolan-5-yl)-(1H)-pyrimidin-2-one.

63. An article of manufacture according to claim 61, wherein said agent is an acyclic nucleoside, an interferon, a renal excretion inhibitor, a nucleoside transport inhibitor, a 2',3'-dideoxynucleoside, an immunomodulator, erythropoietin, ampligen, thyomodulin, thymopentin, foscarnet, ribavirin, or an inhibitor of HIV binding to CD4.

64. An article of manufacture according to claim 61, wherein said agent is an acyclic nucleoside, an interferon, a renal excretion inhibitor, a nucleoside transport inhibitor, a 2',3'-dideoxynucleoside, an immunomodulator, erythropoietin, ampligen, thyomodulin, thymopentin, foscarnet, ribavirin, or an inhibitor of HIV binding to CD4.

* * * * *

UNITED STATES PATENT AND TRADEMARK OFFICE
CERTIFICATE OF CORRECTION

PATENT NO. : 6,180,639 B1
APPLICATION NO. : 07/835964
DATED : January 31, 2001
INVENTOR(S) : Jonathan A. Coates et al.

It is certified that error appears in the above-identified patent and that said Letters Patent is hereby corrected as shown below:

Column 18, line 17, reads "human a phar-" should read -- human --
Column 18, line 18, reads "maceuitcal composition comprising: a compound" should read -- a compound --
Column 18, line 21, reads "thereof, another agent having antiviral activiy, and" should read -- thereof and --
Column 18, line 22, reads "carrier, and" should read -- carrier--
Column 18, line 25, reads "present in said composition is" should read -- present is --
Column 18, line 27, reads "thereof." should read -- thereof, and another agent having antiviral activity. --
Column 18, line 43, reads "wherein said compo-" should read --wherein --
Column 18, line 44, reads "sition contains an amount of the (+)-enantiomer of" should read -- the amount of the (+)-enantiomer is --
Column 18, line 46, reads "wherein said compo-" should read -- wherein --
Column 18, line 47, reads "sition contains an amount of the (+)-enantiomer of" should read --the amount of the (+)-enantiomer is --
Column 19, line 62, reads "wherein said com-" should read --wherein --
Column 19, line 63, reads "position contains an amount of the (+)-enantiomer of" should read -- the amount of the (+)-enantiomer is --
Column 19, line 65, reads "wherein said com-" should read --wherein --
Column 19, line 66, reads "position contains and amount of the (+)-enantiomer of" should read -- the amount of the (+)-enantiomer is --
Column 20, line 1, reads "wherein said corn-" should read -- wherein --
Column 20, line 2, reads "position contains an amount of the (+)-enantiomer of" should read -- the amount of the (+)-enantiomer is --
Column 20, line 4, reads "wherein said corn-" should read -- wherein --
Column 20, line 5, reads "position contains an amount of the (+)-enantiomer of" should read -- the amount of the (+)-enantiomer is --
Column 20, line 43, reads "human a phar-" should read --human --
Column 20, line 44, reads "maceuitcal composition comprising: a compound" should read -- a compound --
Column 20, line 47, reads "thereof, and another agent having antiviral activiy," should read -- thereof, --
Column 20, line 50, reads "present in said composition is" should read -- is --
Column 20, line 52, reads "thereof." should read -- thereof, and another agent having antiviral activity. --
Column 20, line 53, reads "said comp" should read -- said --

UNITED STATES PATENT AND TRADEMARK OFFICE
CERTIFICATE OF CORRECTION

PATENT NO.         : 6,180,639 B1                                                    Page 2 of 2
APPLICATION NO. : 07/835964
DATED              : January 31, 2001
INVENTOR(S)       : Jonathan A. Coates et al.

It is certified that error appears in the above-identified patent and that said Letters Patent is hereby corrected as shown below:

Column 20, line 54, reads "position contains" should read -- compound is --

Signed and Sealed this

Twenty-first Day of November, 2006

JON W. DUDAS
*Director of the United States Patent and Trademark Office*

UNITED STATES PATENT AND TRADEMARK OFFICE
CERTIFICATE OF CORRECTION

PATENT NO.       : 6,180,639 B1
APPLICATION NO.  : 07/835964
DATED            : January 30, 2001
INVENTOR(S)      : Jonathan A. Coates et al.

It is certified that error appears in the above-identified patent and that said Letters Patent is hereby corrected as shown below:

Column 18, line 17, reads "human a phar-" should read -- human --
Column 18, line 18, reads "maceuitcal composition comprising: a compound" should read -- a compound --
Column 18, line 21, reads "thereof, another agent having antiviral activiy, and" should read -- thereof and --
Column 18, line 22, reads "carrier, and" should read -- carrier--
Column 18, line 25, reads "present in said composition is" should read -- present is --
Column 18, line 27, reads "thereof." should read -- thereof, and another agent having antiviral activity. --
Column 18, line 43, reads "wherein said compo-" should read --wherein --
Column 18, line 44, reads "sition contains an amount of the (+)-enantiomer of" should read -- the amount of the (+)-enantiomer is --
Column 18, line 46, reads "wherein said compo-" should read -- wherein --
Column 18, line 47, reads "sition contains an amount of the (+)-enantiomer of" should read --the amount of the (+)-enantiomer is --
Column 19, line 62, reads "wherein said com-" should read --wherein --
Column 19, line 63, reads "position contains an amount of the (+)-enantiomer of" should read -- the amount of the (+)-enantiomer is --
Column 19, line 65, reads "wherein said com-" should read --wherein --
Column 19, line 66, reads "position contains and amount of the (+)-enantiomer of" should read -- the amount of the (+)-enantiomer is --
Column 20, line 1, reads "wherein said corn-" should read -- wherein --
Column 20, line 2, reads "position contains an amount of the (+)-enantiomer of" should read -- the amount of the (+)-enantiomer is --
Column 20, line 4, reads "wherein said corn-" should read -- wherein --
Column 20, line 5, reads "position contains an amount of the (+)-enantiomer of" should read -- the amount of the (+)-enantiomer is --
Column 20, line 43, reads "human a phar-" should read --human --
Column 20, line 44, reads "maceuitcal composition comprising: a compound" should read -- a compound --
Column 20, line 47, reads "thereof, and another agent having antiviral activiy," should read -- thereof, --
Column 20, line 50, reads "present in said composition is" should read -- is --
Column 20, line 52, reads "thereof." should read -- thereof, and another agent having antiviral activity. --
Column 20, line 53, reads "said comp" should read -- said --

UNITED STATES PATENT AND TRADEMARK OFFICE
CERTIFICATE OF CORRECTION

PATENT NO.        : 6,180,639 B1
APPLICATION NO.   : 07/835964
DATED             : January 30, 2001
INVENTOR(S)       : Jonathan A. Coates et al.

It is certified that error appears in the above-identified patent and that said Letters Patent is hereby corrected as shown below:

Column 20, line 54, reads "position contains" should read -- compound is --

This certificate supersedes Certificate of Correction issued November 21, 2006.

Signed and Sealed this

Ninth Day of January, 2007

JON W. DUDAS
*Director of the United States Patent and Trademark Office*